United States Patent
Dewaele et al.

(10) Patent No.: US 6,269,177 B1
(45) Date of Patent: Jul. 31, 2001

(54) METHOD FOR RECONSTRUCTING RADIATION IMAGE OF A BODY FROM PARTIAL RADIATION IMAGES

(75) Inventors: Piet Dewaele, Berchem; Piet Vuylsteke, Mortsel, both of (BE)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 09/201,978

(22) Filed: Dec. 1, 1998

(30) Foreign Application Priority Data

Dec. 1, 1997 (EP) .................................................. 97203766

(51) Int. Cl.$^7$ ....................................................... G06K 9/00
(52) U.S. Cl. ................................................................ 382/131
(58) Field of Search ..................................... 382/128, 130, 382/131, 132, 277, 284, 291; 378/4, 7, 63, 86, 87, 88, 89, 90, 147, 154, 156, 159, 162, 163, 164, 165

(56) References Cited

U.S. PATENT DOCUMENTS

| | | | |
|---|---|---|---|
| 4,876,509 | * 10/1989 | Perlmutter | 324/309 |
| 5,686,960 | * 11/1997 | Sussman et al. | 348/218 |
| 5,706,416 | * 1/1998 | Mann et al. | 345/427 |
| 5,712,890 | * 1/1998 | Spivey et al. | 378/37 |
| 5,933,547 | * 8/1999 | Dudon et al. | 382/300 |

OTHER PUBLICATIONS

"Digital Image Warping", Section 3.6, by George Wolberg, IEEE, 1990, Dr. Dobb's Journal essential books on graphics programming.*

"Correccting Chromatic Aberrations using Image Warping", By George Wolberg et al., IEEE, 1992.*

* cited by examiner

Primary Examiner—Andrew W. Johns
Assistant Examiner—Shervin Nakhjavan
(74) Attorney, Agent, or Firm—Schmeiser, Olsen & Watts

(57) ABSTRACT

A radiation image of a body is reconstructed from original partial radiation images, each comprising part of the radiation image of said body, and part of a radiation image of a geometrical calibration grid the radiation image of which was superimposed on the radiation image of the body. The original partial radiation images are geometrically corrected before being stitched.

7 Claims, 5 Drawing Sheets

Figures 3A, 3B, 3C:
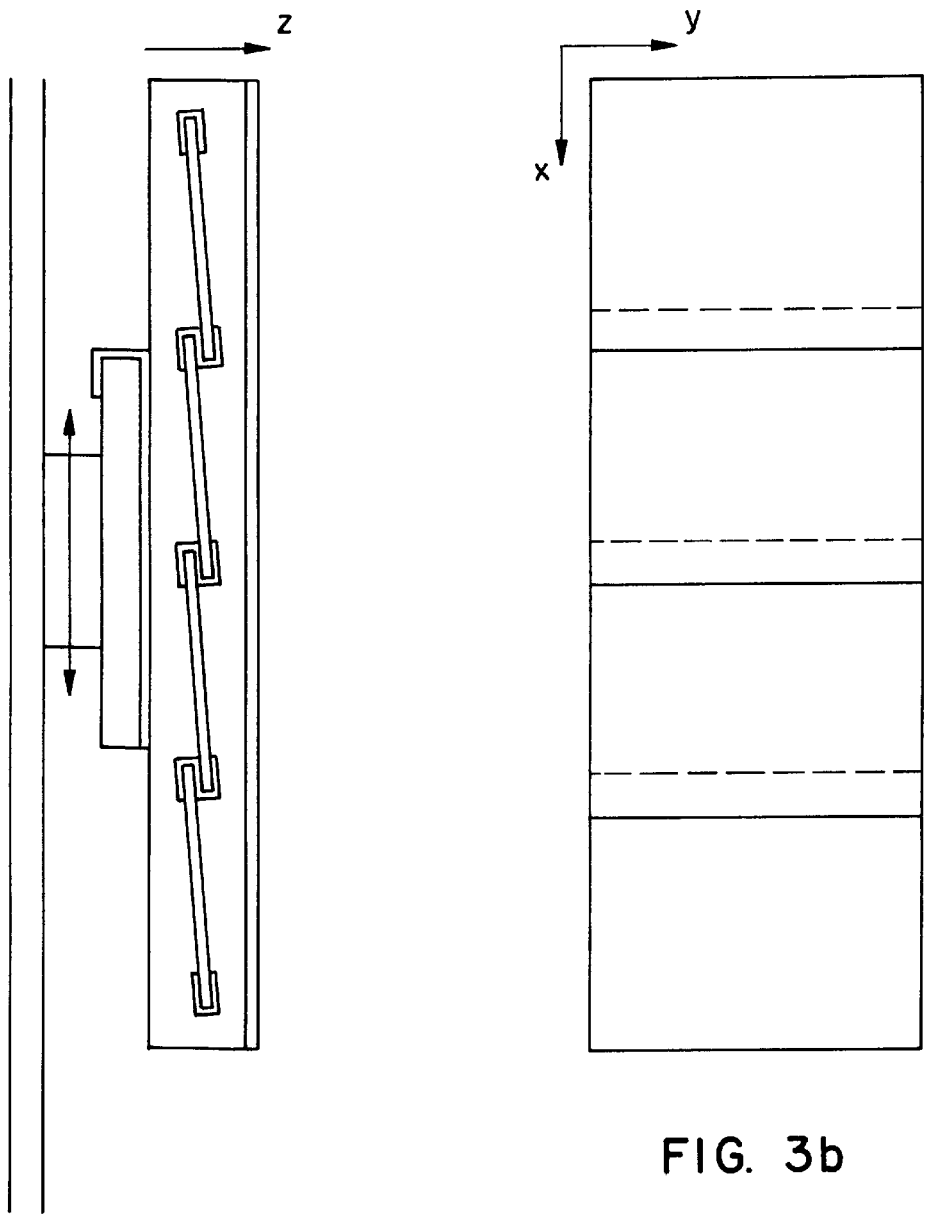

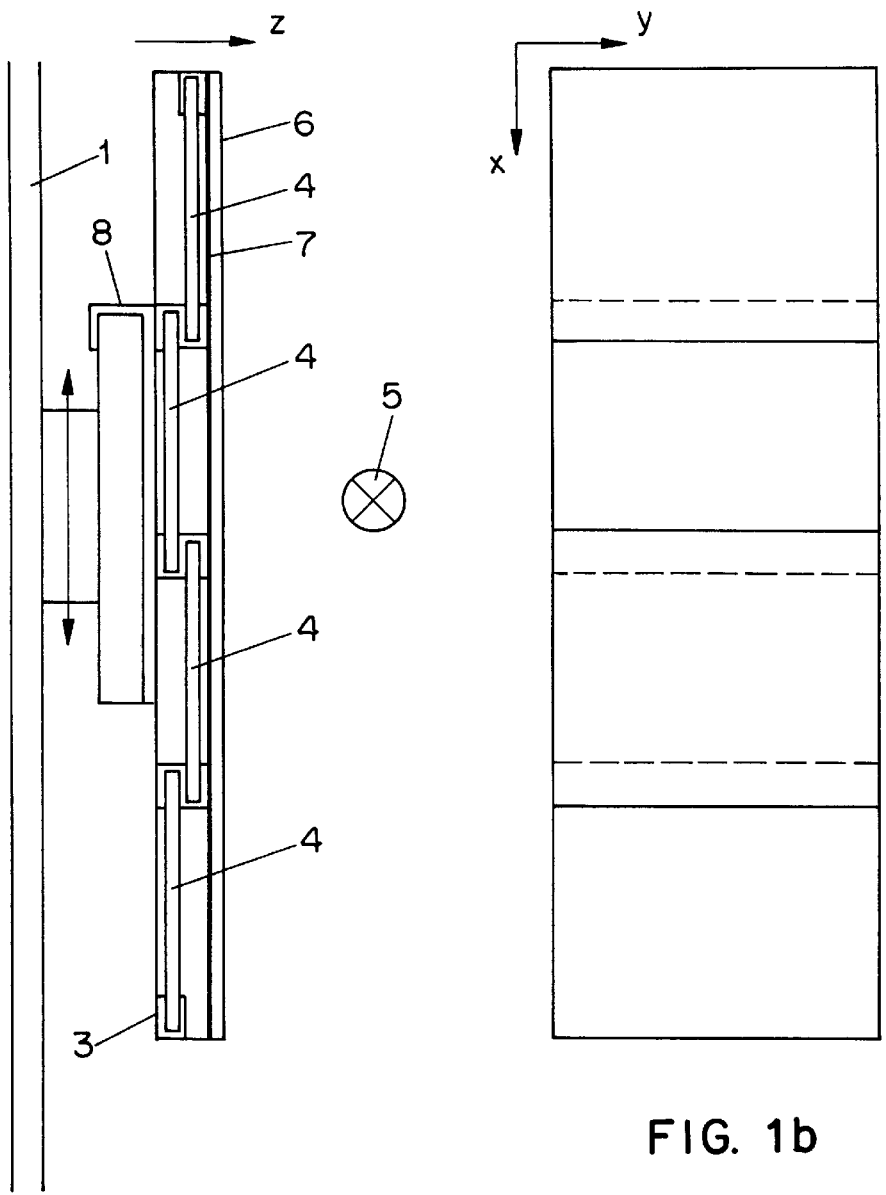
FIG. 1a
FIG. 1b
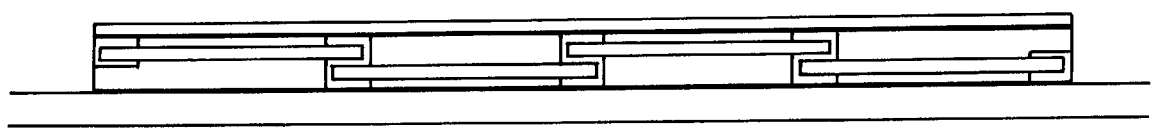
FIG. 1c

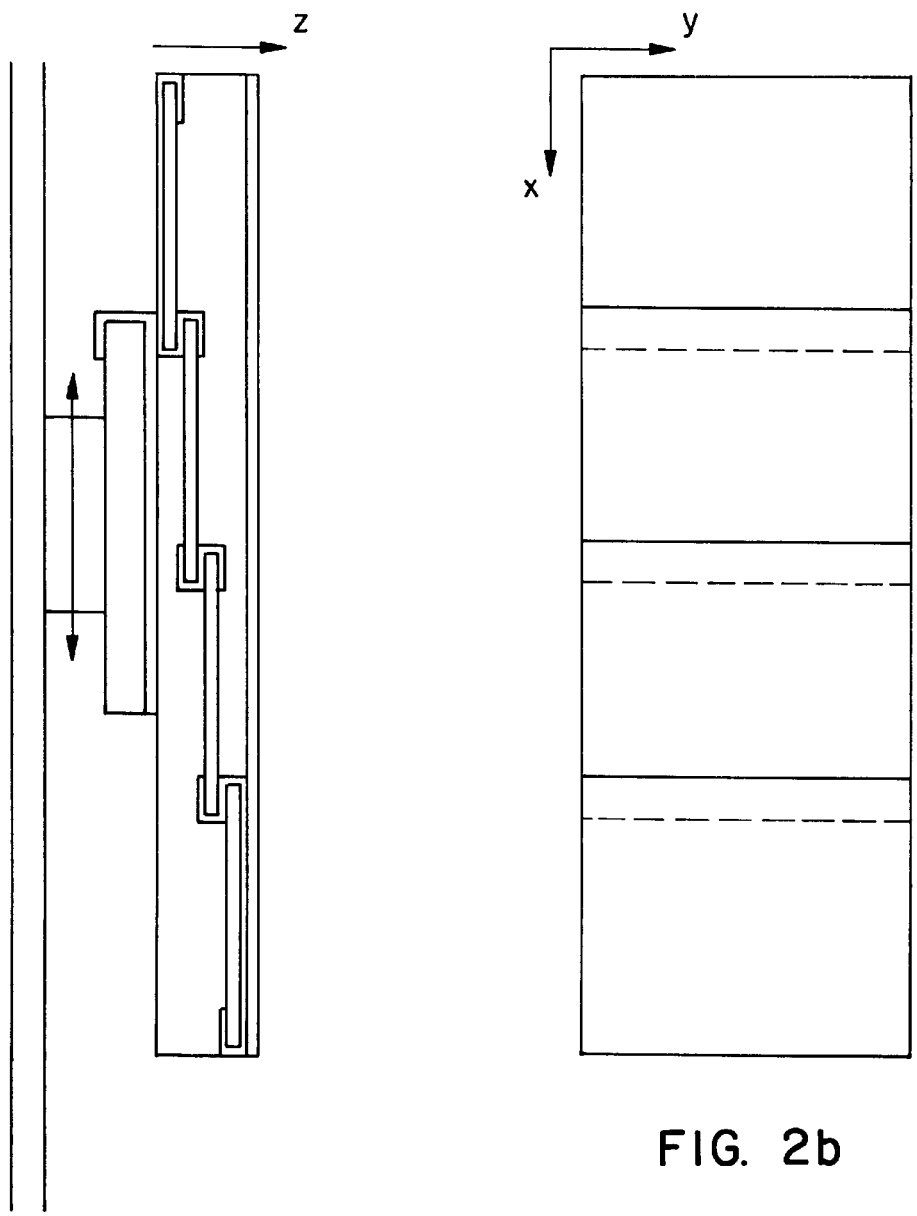
FIG. 2b
FIG. 2a
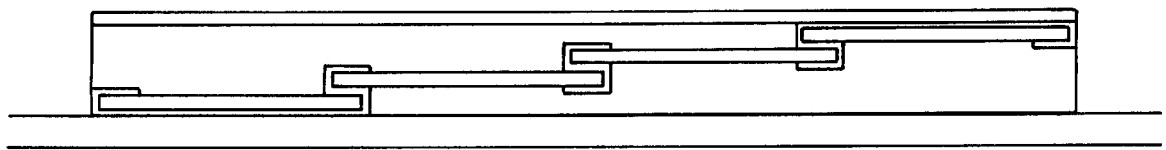
FIG. 2c

METHOD FOR RECONSTRUCTING RADIATION IMAGE OF A BODY FROM PARTIAL RADIATION IMAGES

FIELD OF THE INVENTION

The invention relates to a method for reconstructing a radiation image of a body from partial radiation images each comprising part of the radiation image of said body.

BACKGROUND OF THE INVENTION

In flat projection radiography examination types exist that aim at imaging a larger portion of the body than can be fit on a single, even the largest imaging cassette.

Such imaging needs arise in so-called full-leg or full-spine examinations, where clinical indication requires that e.g. the full spine or the full leg is examined at once so as to enable or to quantify diagnosis.

Analogous to conventional film-screen based radiography, in storage phosphor image acquisition wherein a radiation image is temporarily stored in a photostimulable phosphor screen, such examinations are achieved by filling a larger cassette with a plurality of storage phosphor screens, generally overlapping with one another so as to completely cover the longer, elongate cassette (an embodiment referred to as an overlapping sheet embodiment).

Such elongate cassettes are typically 35×105 cm for full-leg examinations and 30×90 cm for full-spine examinations. In the overlapping sheet embodiment, the largest single film cassette measures 35×43 cm and hence is unsuitable for imaging the spinal column or a leg. Typically, 4 screens are used, e.g. 4 (24×30 cm) screens are arranged in a 30×90 cm cassette, clearly resulting in an overlap configuration. Therefore, the part of the image corresponding to the overlap zone, will be less exposed.

Alternatively, the situation of non-overlapping images may also occur, e.g. in a configuration of 3 (35×35 cm) imaging screens in a 35×105 cm cassette, resulting in 3 pair-wise touching but otherwise non-overlapping images.

During exposure, a fixed grid is simultaneously present in the path of the X-ray beam, resulting in an image of a raster of horizontal and vertical parallel thin lines superposed to the radiation image of the elongate body. These lines aid the radiologist or operator in reconstructing the original geometry of the body, since lines on image must necessarily extend continuously and seamlessly into lines of the previous image and the next image.

In European patent application EP-A-97 200 857 and in U.S. Ser. No. 09/035,528, a method is disclosed to acquire a radiation image of an elongate body by using a sequence of recording members in partially overlapping disposition.

The image acquisition process assumes the use of an elongate cassette in which a sequence of stimulable phosphor screens are arranged in an overlapping manner so as to completely cover the cassette.

After exposure, the elongate cassette is opened, the individual screens are removed from the cassette and are each put into a smaller cassette of a size corresponding to the dimensions of an individual screen. Then, the cassettes are sequentially fed into a dedicated read-out apparatus where the cassette is again opened, the screen is taken out of the cassette, and scanned by means of stimulating radiation. The image-wise modulated light that is emitted upon stimulation is detected and converted into a digital image representation of part of the elongate body. Next, the digital image representations read out of each of the cassettes are recombined to form an image of the entire elongate body.

This patent application further relates to a method to obtain a single 'stitched' image of an elongate body using the images read out of each of these recording members.

Patent applications EP-A-97 200 857 and U.S. Ser. No. 09/035,528 further disclose a method to obtain a 'stitched' image of the elongate body, i.e. a method is disclosed for recombining the image representations read out of each of the cassettes into a complete image of the elongate body.

The method makes use of the image of a periodic grid which was placed on top of the elongate cassette in the path of irradiation so that it covers the full length of the cassette in a continuous way. The image of the grid was thus superimposed on the image of the elongate body which was recorded on the overlapping recording members. Since the grid covers the full length of the cassette (or of the elongate body) in a continuous way, its image should also be present in the resulting re-constructed image composition in a continuous way. This knowledge was used to enable alignment and stitching of the images with respect to each other.

The stitching method disclosed in above patent applications depends on two basic algorithms: (1) detection and modelling of the periodic grid and (2) cross-correlation of overlapping image parts. The disclosed stitching method deals with corrections for image distortions due to shift, overlap and rotation of a sub-image with respect to the previous and next sub-image.

It may however occur that the image of the attenuating grid or part thereof on a recording member is deformed relative to the original form of the grid. This means that parts of the image of the calibration grid are not congruent with the original physical grid. Since the image of the grid is used as a guidance for reconstructing the entire image of the elongate body from the partial images read out of the individual recording members, such deformation is unacceptable because it might lead to erroneous stitching.

Such problems have not been dealt with in the prior art teachings.

OBJECTS OF THE INVENTION

It is thus an object of the present invention to provide a method of reconstructing a radiation image of a body from partial radiation images, which overcomes stitching problems originating from geometrical deformation of the partial images.

Further objects of this invention will become apparent from the description hereafter.

SUMMARY OF THE INVENTION

The above-mentioned objects are realised by a method for reconstructing a radiation image of a body from original partial radiation images, each comprising part of the radiation image of said body and part of a radiation image of a geometrical calibration grid superimposed on the radiation image of said body, characterised in that said original partial radiation images are geometrically corrected so as to obtain geometrically corrected partial images, said geometrically corrected partial images are stitched so as to form said radiation image of said body.

In a specific embodiment the geometrically corrected partial images are obtained by subjecting the original partial images to a geometric transformation so that the parts of the radiation image of said geometric calibration grid are restored to the geometry of the geometrical calibration grid and so that simultaneously the parts of the radiation image of the body are restored to the geometry of the original parts of the radiation image.

Further details of the present invention will be explained with reference to a specific embodiment wherein an image of an elongate body such as a full leg-full spine image, is reconstructed from partial images each representing a part of the elongate body. The partial images are read out of separate recording members that are each conveyed in a separate cassette, these separate cassettes being assembled into one of the arrangements described below. The recording members are for example photostimulable phosphor screens, but other embodiments such as a film-intensifying screen combinations may be envisaged.

By the use of cassettes, the individual screens need no longer to be handled in dark room conditions and the risk of accidental damaging of the screens or dust contamination is eliminated since the screens are no longer taken out of the cassettes.

However, since such cassettes have a thickness that is not negligible and since cassettes may be in a tilted position, the image of a calibration grid which is placed on top of the assembly might be geometrically deformed relative to the form of the physical grid. Such deformation problems are solved by the method of the present invention.

It will be clear that this invention is not limited to the reconstruction of an image of an elongate body, nor to the recording media described higher, nor to an arrangement wherein recording media are conveyed in individual cassettes that are together assembled into a cassette-arrangement.

The present invention is applicable to all kinds of images that are reconstructed from a number of partial images (e.g. acquired by means of a two-dimensional arrangement of (overlapping) cassettes).

In order to be able to exactly reconstruct the entire image of a body from partial images, a pattern of reference marks, in the following called a 'geometrical calibration grid' is recorded onto the radiation sensitive recording members in addition to the image of the body.

A geometrical calibration grid may take several forms. It may for example exist of an arrangement of reference marks the relative position of which is known. However, a grid made of equidistant lines of radiation attenuating material which covers the entire length of the cassette arrangement is preferred for the ease of manipulation, detection and recomposition.

During exposure, the grid is present in the path of the X-ray beam, resulting in an image of a raster of horizontal and vertical parallel thin lines superposed to the radiation image of the elongate body. Lines in the image must necessarily extend continuously and seamlessly into lines of the previous image and the next image. The image of the grid may thus guide the radiologist in reconstructing the image and as will be explained further on.

BRIEF DESCRIPTION OF THE INVENTION

Figure 4:
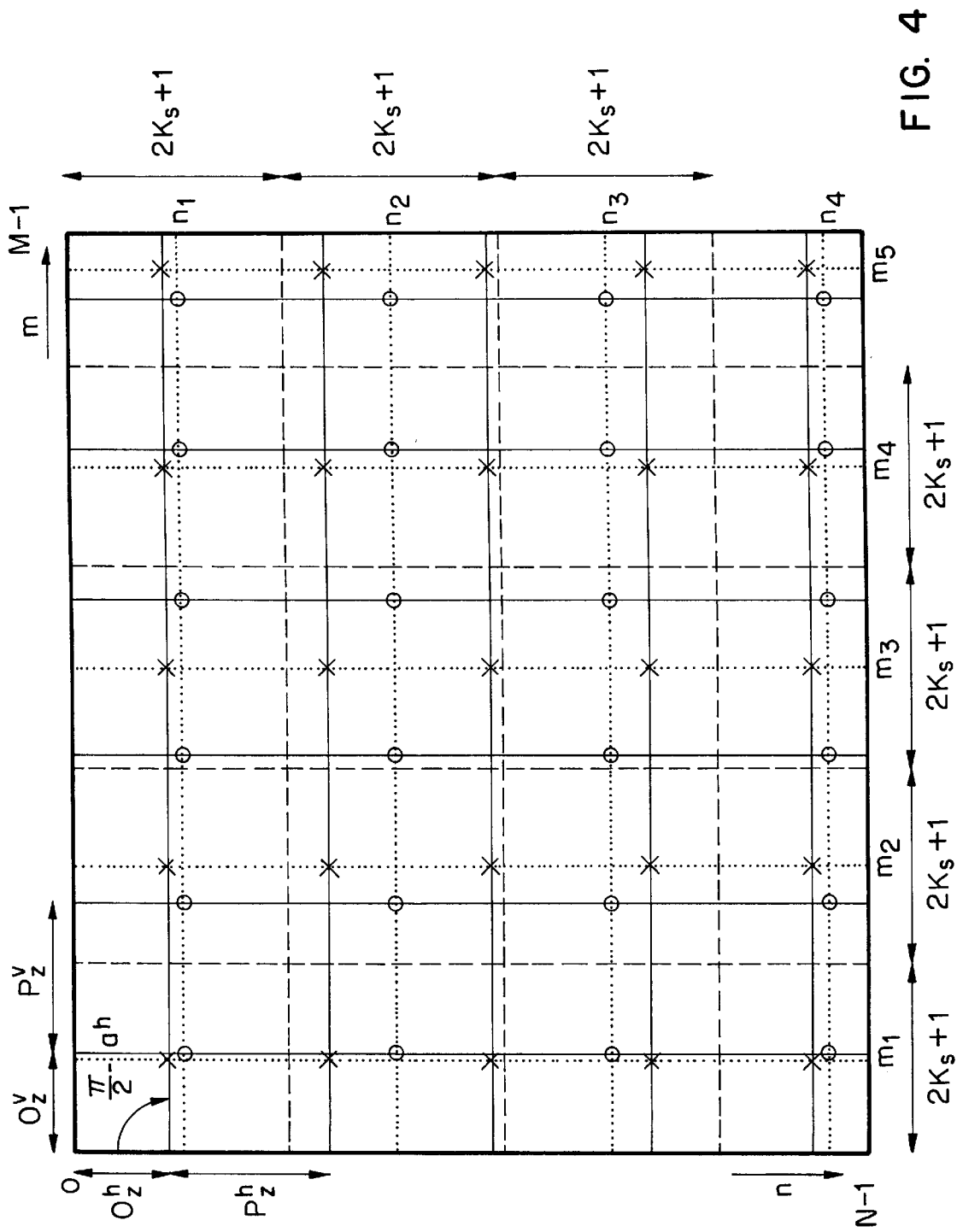
Figure 5:
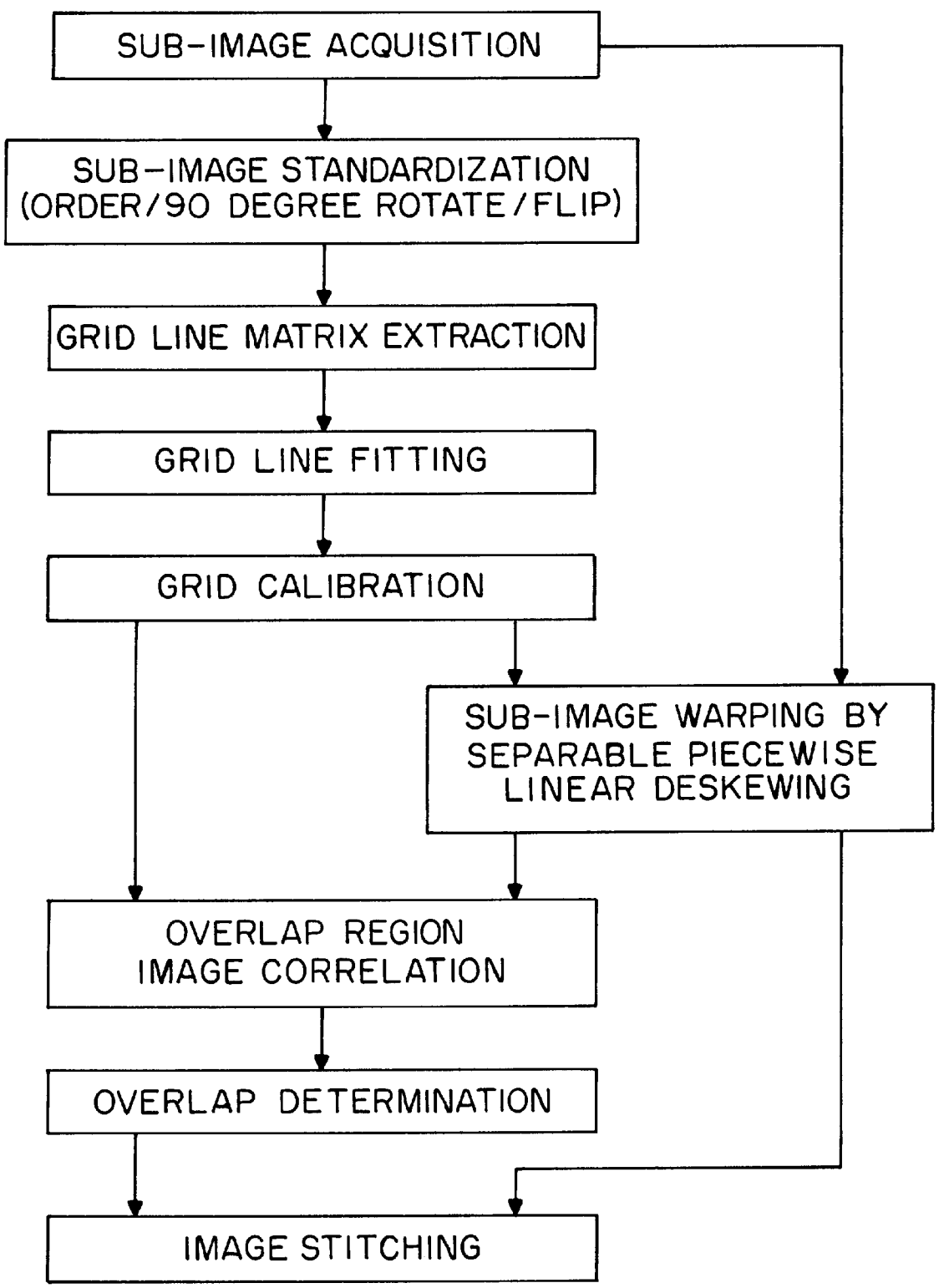

Further advantages and embodiments of the present invention will-become apparent from the following detailed description illustrated by means of the following drawings wherein FIG. 1 depicts a mechanical set up for the acquisition of an image of an elongate body using a plurality of regular size cassettes in an alternating overlapping disposition, FIG. 2 depicts a mechanical set-up for the acquisition of an image of an elongate body using a stack of regular size cassettes in a staircase overlapping disposition, FIG. 3 depicts a mechanical set-up for the acquisition of an image of an elongate body using a stack of regular size cassettes in an oblique overlapping disposition, FIG. 4 depicts a grid imprint (solid lines) in one of the acquired sub-images obtained by the method of oblique overlapping disposition. Each of the overlapping cassettes creates a geometric distortion thereby generating non-congruent 4-sided polygons. Other deformations may be present, e.g. the grid may further be rotated with respect to the image borders either due to rotation of the screen in the regular size cassette, or due to rotation of the screen with respect to the scanning axis in the read-out apparatus or due to a combination of said misalignments. The dashed lines ( - - - ) denote subdivision into rectangular vertical and horizontal blocks for profile calculation, the dotted lines ( . . . ) denote the centre lines of the corresponding blocks. The hole marks (o) denote the positions of the vertical grid lines in the horizontal profiles, the cross marks (x) denote the positions of the horizontal grid lines in the vertical profiles, FIG. 5 is a block diagram illustrating the different steps of the algorithm.

DETAILED DESCRIPTION OF THE INVENTION

While the present invention will hereinafter be described in connection with preferred embodiments thereof, it will be understood that it is not intended to limit the invention to those embodiments.

The present invention is illustrated by means of an embodiment wherein an X-ray image of e.g. a full spine of a patient is recorded on a number of photostimulable phosphor screens. On each of these screens another part of the image of the spine is recorded.

Each of the screens are conveyed in a regular size cassette having dimensions which correspond to the dimensions of the individual screen.

The screens are supported in a staggered disposition, in this example a partially overlapping staggered disposition, so that the elongate dimension of the assembly of the cassettes is at least as long as the elongate dimension (the length) of the elongate body.

In this way an X-ray image of the elongate body can be recorded in a single exposure onto the recording members in the assembly of cassettes.

FIGS. 1,2,3 depict different configurations of an assembly of a plurality of Z cassettes, each cassette holding a recording member. These figures also show a mechanical set up for holding such an assembly.

An assembly comprises a rigid support 3. Several cassettes 4 can be attached to or inserted in support 3, such that each cassette partially overlaps with its predecessor and/or successor cassette.

An assembly may comprise a front panel 6 at the tube side of the support. Such a front panel may hold a density attenuating (rectangular) grid and/or an anti-scatter grid, both indicated schematically by vertical line 7.

The front side (side directed to the X-ray tube which is schematically indicated by numeral 5) of the front panel 6 is made of X-ray transparent material so as not to absorb any radiation.

A standard wall bucky X-ray recording apparatus 1 used for recording a radiation image of a patient is shown in these figures.

The rigid support 3 is mounted in the vertical position to the bucky for vertical patient postures. The support can be hooked into the wall bucky X-ray recording apparatus by hook 8.

Alternatively, the support holding the cassettes can be positioned horizontally (on an exposure table or on the floor) for horizontal postures.

The exact disposition of cassettes on the support is disclosed in detail in the following.

Also the consequences of using cassettes instead of recording members in staggered disposition are explained.

In contrast to the situation disclosed in patent application EP-A-97 200 857 and in U.S. Ser. No. 09/035,528, where a single elongate cassette is used for image recording, the cassette comprising a number of partially overlapping recording members such as photostimulable phosphor screens or screen-film combinations and where the thickness of the individual recording members is small and negligible, the thickness of the individual cassettes in this invention is not negligible with regard to deformations of an image of the attenuating (rectangular) grid.

This image of the attenuating rectangular grid is used as a guidance for reconstructing the entire image of the elongate body from the partial images read out of the individual recording members that each carry a part of the image of the elongate body.

Because the recording members are not co-planar, the projection of the rectangles of the attenuating grid is different for each screen and is governed by three-dimensional projective geometry equations.

For the purpose of clarification, a world co-ordinate system (x,y,z) is defined such that the x-axis and y-axis point in the vertical and horizontal direction and the z-axis points in the direction perpendicular to the image plane (parallel to the path of X-ray incidence).

In the context of this invention three workable dispositions are considered; other combinations may be thought of without departing from the aim and scope of the current invention.

In the first disposition, depicted in FIG. 1 the recording members are perfectly parallel to the attenuating grid plane and their distance to the attenuation grid plane alternates between successive recording member. The larger the distance between a recording members and the attenuating grid, the larger the magnification of the projected grid rectangles will be. However, there is no projective distortion (the projective grid lines remain parallel).

In order to cover the entire elongate body, a plurality of cassettes is used in an overlapping disposition.

The situation is shown in FIGS. 1b, 2b, and 3b. Hidden borders of sub-images (sub-images or partial images are images of part of the elongate body recorded on a recording member in an individual cassette) are represented by a dashed line, visible sub-image borders by a continuous line.

Because of an alternating zoom factor between odd and even numbered recording members, this situation is referred to as the alternating overlapping disposition.

The second disposition, shown in FIG. 2, shows a staircase of overlapping recording members. The situation differs from the foregoing in that, except for the last sub-image, each sub-image will have its bottom part attenuated by the next recording member. Therefore, the overlap area can be treated in a uniform way throughout the image composition process. However, the zoom factor caused by the stepwise increasing distance between recording member plane and attenuating grid plane, is different for each recording member; the sub-images acquired by the farthest recording members may therefore need relatively significant down-zooming, or conversely, the sub-images acquired by the nearest recording members may need relatively significant up-zooming. This case is referred to as the staircase overlapping disposition.

The third case, depicted in FIG. 3 is a compromise between the drawbacks of the former two cases. It shows a sequence of slightly tilted recording members, the tilt angle being defined as a function of the ratio of recording member thickness to height, so that the resulting disposition fits in a minimal and perfectly vertical housing. This disposition features both uniform overlap configuration for each recording member and an identical projective distortion geometry. The projective distortion geometry is different from a simple zooming (magnification or reduction), however. Running from top to bottom, the vertical inter-line distance undergoes a linear increasing or decreasing zooming, depending on whether the tilt angle is positive or negative respectively. However, this projective distortion is equal for all imaging screens. For the disposition case depicted in FIG. 3, the inter-line distance decreases from top to bottom as schematised in FIG. 4. This acquisition modality is referred to as the oblique overlapping disposition.

For all cases presented, the recording members are mounted in a detachable mechanical set-up to which the attenuation grid and anti-scatter grid can be fixed, enabling to put the ensemble on an exposure table or on the ground for horizontal postures. The corresponding horizontal dispositions are depicted in FIG. 1c, FIG. 2c, FIG. 3c.

All dispositions shown in FIGS. 1, 2, 3 have overlapping cassettes. Dispositions with touching or separate non-overlapping cassettes may be thought of likewise. They are sub-optimal solutions because even in case of a touching disposition, the thickness of the housing of the recording member prevents the diagnostic area from being covered completely by the area of the recording member.

In addition to the three-dimensional projective geometry distortions caused by the three-dimensional physical disposition of the screens with respect to the attenuating grid, the distortions coped with in patent application EP-A-97 200 857 and in U.S. Ser. No. 09/035,528 remain equally well present.

For sake of clarity, these classic distortions are summarised below:

shift (y-axis dislocation) of a sub-image with respect to the next or previous sub-image, overlap (in the x-axis) of a sub-image with respect to the next or previous sub-image, rotation of the grid of one sub-image with respect to the grid of the next or previous sub-image, the angle of said rotation being the combined result of (1) the non-perfect alignment of the borders of the recording member with respect to the perfectly horizontal and vertical axis, in the assumption that the attenuating grid lines are placed perfectly horizontally and vertically; (2) the non-perfectly straight feed-through in the digitising apparatus of the recording member.

In order to use the aforementioned recording process depicted in FIGS. 1,2,3, a suitable image processing method is therefore required to compensate not only for said projective geometry distortions, but also for the classical distortions dealt with in patent application EP-A-97 200 857 and in U.S. Ser. No. 09/035,528.

FIG. 4 shows a schematic representation of the grid recorded on one of the sub-images, with definition of co-ordinate axes and key quantities. The image has been acquired by the method of oblique overlapping disposition of recording members and hence the interline distance of vertically running grid lines narrows from top to bottom. The inter-line distance of horizontally running grid lines remains constant. However, the algorithm disclosed hereafter is able to cope with deformations of grid lines from the perfectly vertical and the perfectly horizontal simultaneously. The co-ordinate system's origin is in the upper left corner, with co-ordinate m running inside a row from left to right along different columns (in the horizontal direction), co-ordinate n running from top to bottom along different rows (in the vertical direction). The solid lines represent the imprint of the attenuating grid onto the image. In general, the raster formed by the grid lines can be tilted with an angle $\alpha^h$ with respect to the horizontal axis. The rotation is due either to a rotated position of the recording member (e.g. an image screen) with respect to the cassette physical borders, or to a non-perfectly straight screen feed-through in the digitising apparatus, or a combination of both. Obviously, the resulting rotation angle $\alpha^h$ is small.

Basic to the operations is the detection and characterisation of the contrasting grid which produces a rectangular pattern of less exposed pixels in each of the sub-images $S_z$, $z=1 \ldots Z$. $Z$ is the total number of images to be stitched and is typically 3 or 4. The method however generalises to any actual number of sub-images. The pattern formed by the grid in sub-image $S_z$ is fully characterised by the knowledge of (1) the period $P_z^h$ and $P_z^v$ between the gridlines in horizontal resp. vertical direction, (2) line equations of the individual horizontal and vertical grid lines as disclosed by the current invention and (3) the offset $O_z^h$ and $O_z^v$ of horizontal and vertical gridlines with respect to the horizontal image border and the vertical image border respectively. Knowledge of the sets of these parameters is a necessary and sufficient condition for the reconstruction of the grid in the sub-images and for forming a composed total image of an elongate body part by image stitching.

In the sequel, (i,j), (m,n) or (x,y) denote image co-ordinates, (M,N) denote the image dimensions. It is assumed without loss of generality that all sub-images have equal dimensions.

FIG. 5 depicts the general flow of operations, the steps of which are further commented.

Grid Line Matrix Extraction

This step covers all low-level operations such as disclosed in patent application EP-A-97 200 857 and in U.S. Ser. No. 09/035,528, the contents of these patent applications being incorporated by reference, to extract the positions of grid lines in blocks of integrated line profiles. The output of this step is a sequence of m respectively n co-ordinates denoting the positions of the circles respectively crosses in FIG. 4.

Grid Line Fitting

As a result of method disclosed in patent application EP-A-97 200 857 and in U.S. Ser. No. 09/035,528, two grid matrices are obtained, $g^h$ for the horizontal resp. $g^v$ for the vertical direction, storing the indexes of all grid lines detected in such a manner that the resulting arrangement of non-zero entries in a column of $g^h$ resp. a row of $g^v$ all correspond to the row resp. column locations of the same physical grid line. By denoting with $Q_h$ and $Q_v$ the number of blocks in the horizontal resp. vertical direction and denoting the number of detected grid lines in the sequences $G^h$ and $G^v$ by $N_{g^h}$ resp. $M_{g^v}$, the dimensions of $g^h$ resp. $g^v$ are $Q^h \times N_{g^h}$ resp. $Q^v \times M_{g^v}$, such that there are $N_{g^h}$ horizontally oriented grid lines detected and $M_{g^v}$ vertically oriented grid lines detected. The sequences of grid line co-ordinates are input to a line fitting step so as to model each grid line with the equation of a straight line. To this purpose, the row resp. column co-ordinates of the grid matrices $g^h$ and $g^v$ are subjected to a linear regression, commonly known in the prior art such as T. Pavlidis, Algorithms for Graphics and Image Processing, Computer Science Press, 1982, pp. 281–292, Polygonal Approximations. Each linear regression results in the offset and slope of the fit line corresponding to a grid line. For the $N_{g^h}$ horizontally oriented grid lines there are $Q_h$ data points to a fit a line to, for the $M_{g^v}$ vertically oriented grid lines there are $Q_v$ data points available for fitting. The equations of the resulting horizontally resp. vertically oriented fit lines are $$L_{l^h}^{h,z}(m) = \alpha_{l^h}^{h,z} m + \beta_{l^h}^{h,z}$$

$l^h = 0 \ldots N_{g^h} - 1$
$z = 1 \ldots Z$ $$L_{l^v}^{v,z}(n) = \alpha_{l^v}^{v,z} n + \beta_{l^v}^{v,z}$$

$l^v = 0 \ldots M_{g^v} - 1$
$z = 1 \ldots Z$ in which the coefficients $\alpha$ and $\beta$ are the slope and the axis offset of the fit lines. Obviously, any other parameterizable curve could model the grid lines, depending on the nature of the projective geometry distortion. However, because of the pinhole X-ray illumination and the planar geometric disposition of recording member with respect to grid plane, straight lines remain straight lines under projection, so that straight line fitting effectively models the grid line data points.

Grid Calibration and Deformation Measurement

The line equations of the grid lines in each sub-image serve as input to determine the final position of the grid line in the stitched image. Each horizontally running grid line will be de-skewed so as to become perfectly horizontal, the position of which is determined in this step. Analogously, each vertically running grid line will be de-skewed to be perfectly vertical, the position of which is determined in this step.

Furthermore, the interline distance is made equal to the periodicity distance, for all grid lines running horizontally and vertically in the sub-images. The periodicity distance is derived in the "Grid line matrix extraction" step.

The result of the grid calibration step is that all previously enumerated deformations of the ideal rectangular grid are captured in an associated set of skew line equations, given in the "Grid line fitting" step. The deformations corrected for include shift of one sub-image with respect to the other sub-images, rotation of one sub-image with respect to the other sub-images, varying interline distance due to the zoom effect caused by different image screen-attenuating grid distances, and projective geometry distortions caused by non-parallel screen-grid configurations.

More specifically, the quantity $P^v$ denotes the minimum of all periodicity vectors between vertically running grid lines of the ensemble of Z input sub-images.

$$P^v = \min(P_z^v)$$

$z = 1 \ldots Z$ and will be used to normalise the distance between vertically running grid lines. For a square physical grid, $P^v$ will be used to normalise the distance between horizontally running grid lines as well, so that a perfectly square grid will be reconstructed on completion of the warping process. For a rectangular grid, a similar quantity $P^h$ denotes the minimum of all periodicity vectors between horizontally running grid lines of the ensemble of Z input sub-images.

$$P^h = \min(P_z^h)$$

$z = 1 \ldots Z$

Taking the minimum of the set of periodicity vectors ensures that each warped sub-image will fit the original sub-image size so that no diagnostic information is lost.

The position $\hat{\beta}_0^{v,z}$ of the first vertical warped grid line and the positions of the remaining set of vertically warped grid lines are determined as follows $$\hat{\beta}_0^{v,z} = \frac{1}{Z}\sum_{z=1}^{Z} L_0^{v,z}(N/2)$$

$$\hat{\beta}_{l^v}^{v,z} = \hat{\beta}_0^{v,z} + l^v P^v$$

$l^v = 1 \ldots M_g^v - 1$, which positions are equal for all sub-images $S_z, z=1 \ldots Z$.

The position $\hat{\beta}_0^{h,z}$ of the first horizontally warped grid line and the positions of the remaining set of horizontally warped grid lines is determined as follows $$\hat{\beta}_0^{h,z} = \max(L_0^{h,z}(0), L_0^{h,z}(M-1))$$

$$\hat{\beta}_{l^h}^{h,z} = \hat{\beta}_0^{h,z} + l^h P^h$$

$l^h = 1 \ldots N_g^z - 1$ which positions are different for all sub-images $S_z, z=1 \ldots Z$.

The skew values for the horizontally resp. vertically oriented grid lines are given by $$\Delta^{h,z}(m, \hat{\beta}_{l^h}^{h,z}) = L_{l^h}^{h,z}(m) - \hat{\beta}_{l^h}^{h,z}$$

$l^h = 0 \ldots N_g^h - 1$ $$\Delta^{v,z}(\hat{\beta}_{l^v}^{v,z}, n) = L_{l^v}^{v,z}(n) - \hat{\beta}_{l^v}^{v,z}$$

$l^v = 0 \ldots M_g^v - 1$ for all sub-images $S_z, z=1 \ldots Z$.

Two 2-dimensional warping matrices are defined for the horizontal resp. vertical de-skewing operation by linearly interpolating the skew values for all positions in between two successive grid lines $$\Delta^{h,z}(m, n) = \frac{(n - \hat{\beta}_{l^h}^{h,z})\Delta^{h,z}(m, \hat{\beta}_{l^h+1}^{h,z}) + (\hat{\beta}_{l^h+1}^{h,z} - n)\Delta^{h,z}(m, \hat{\beta}_{l^h}^{h,z})}{P^h} \quad \begin{array}{l} \hat{\beta}_{l^h}^{h,z} \leq n \leq \hat{\beta}_{l^h+1}^{h,z} \\ l^h = 0 \ldots N_g^h - 2 \end{array}$$

$$\Delta^{v,z}(m, n) = \frac{(m - \hat{\beta}_{l^v}^{v,z})\Delta^{v,z}(\hat{\beta}_{l^v+1}^{v,z}, n) + (\hat{\beta}_{l^v+1}^{v,z} - m)\Delta^{v,z}(\hat{\beta}_{l^v}^{v,z}, n)}{P^v} \quad \begin{array}{l} \hat{\beta}_{l^v}^{v,z} \leq m \leq \hat{\beta}_{l^v+1}^{v,z} \\ l^v = 0 \ldots M_g^v - 2 \end{array}$$

for all sub-images $S_z, z=1 \ldots Z$.

Sub-image Warping by Piece-Wise Linear Separable De-Skewing

This module will transform the sub-image such that (1) each vertical fitted grid line is de-skewed to the perfectly vertical target line and the ensemble of all vertical target lines is equidistant; (2) each horizontal fitted grid line is de-skewed to the perfectly horizontal target line and the ensemble of all horizontal target lines is equidistant; (3) the skew applied to each pixel in between the vertical target lines (respectively horizontal target lines) is obtained by linear interpolation of the skew associated with the left (upper) fit line and the right (lower) fit line. Therefore, the total operation is termed image warping since the local displacements are place dependent and performed by piece-wise linear de-skewing, the skew values varying piece-wise linearly along the skew direction and their control points being defined by the skew values associated with the grid fit lines.

Since the skew values are floating point values, the problem of image re-sampling on a discrete grid needs to be addressed. Interpolation is the process of determining the values of a function at positions lying between its samples. Since interpolation reconstructs the signal lost in the sampling process by smoothing the data samples with the interpolation function, an important issue is how image sharpness can be retained at the maximum. The performance of the interpolation in the passband and stopband, the numerical accuracy and the computational cost of interpolating algorithms are therefore dependent on the interpolation kernel. In addition to the choice of the interpolation algorithm, a computational scheme has been devised to integrate the interpolation process in the aforementioned de-skew operation. Sampling theory establishes that the sinc function is the ideal interpolation kernel. Although this interpolation filter is exact, it is not practical since it is an IIR filter defined by a slowly converging infinite sum. The next to optimal interpolating kernel with local extent over 4 points is offered by the interpolating cubic B-spline. The interpolated data value is obtained as followed for the horizontal de-skew operation $$\hat{S}_z^h(m, n) = \sum_{k=-2}^{2} T_z^h(m+k, n) h(\Delta^{h,z}(m, n) + k)$$

with the cubic B-spline interpolating kernel h given by the following piece-wise cubic polynomials, sometimes referred to as the Parzen window $$h(x) = \frac{1}{6}\begin{cases} 3|x|^3 - 6|x|^2 + 4 & 0 \leq |x| < 1 \\ -|x|^3 + 6|x|^2 - 12|x| + 8 & 1 \leq |x| < 2 \\ 0 & 2 \leq |x| \end{cases}$$

with $\Delta^h(m,n)$ the horizontal 2-dimensional skew matrix defined above. The matrix $T_z^h(m,n)$ is obtained by solving the following set of N equations, one set for each row n defined by a tri-diagonal matrix $$\begin{bmatrix} S_z(0, n) \\ S_z(1, n) \\ S_z(2, n) \\ \ldots \\ S_z(m-2, n) \\ S_z(m-1, n) \end{bmatrix} = \begin{bmatrix} 4 & 1 & & & & \\ 1 & 4 & 1 & & & \\ & 1 & 4 & 1 & & \\ & & \ldots & & & \\ & & & 1 & 4 & 1 \\ & & & & 1 & 4 \end{bmatrix} \begin{bmatrix} T_z^h(0, n) \\ T_z^h(1, n) \\ T_z^h(2, n) \\ \ldots \\ T_z^h(m-2, n) \\ T_z^h(m-1, n) \end{bmatrix},$$

$n = 0 \ldots N - 1$

The de-skew operation is executed independently in the horizontal and vertical direction. The result of the output of the horizontal de-skew $\hat{S}_z^h(m,n)$ is input to the vertical de-skew operation using the same de-skew algorithm to produce the final rotated image $\hat{S}_z(m,n)=\hat{S}_z^{hv}(m,n)$. The result image will show the deformed grid geometrically corrected to its original form, that is, as two sets of mutually orthogonal equally spaced perfectly straight and parallel lines. Furthermore, since the offset (distance to the image border) of the first vertical grid line is equal for all sub-images, the operation will ensure the perfect continuity (co-linearity) of the vertically oriented de-skewed grid lines in the image composition. Analogously, the perfect continuity of periodicity of horizontal corrected grid lines is guaranteed by restrictions imposed upon the overlap computation and determination as disclosed in patent application EP-A-97 200 857 and in U.S. Ser. No. 09/035,528.

Other image interpolation schemes are devisable based on prior art such as presented in e.g. G. Wolberg, Digital Image Warping, IEEE Computer Society Press Monograph, 1990.

For example, bi-linear interpolation or separate linear interpolation in two directions can be applied. This interpolation method provides a faster implementation than B-spline interpolation. B-spline interpolation is computationally more expensive but provides a more accurate result.

Overlap Image Correlation

This step proceeds as disclosed in patent application EP-A-97 200 857 and in U.S. Ser. No. 09/035,528, using the warped sub-images and the grid model parameters as input to the process.

Image Stitching

This step proceeds as disclosed in patent application EP-A-97 200 857 and in U.S. Ser. No. 09/035,528, using the warped sub-images and the overlap values as input to the process.

What is claimed is:

1. A method for reconstructing a radiation image of a body from original partial radiation images, comprising:

simultaneously exposing a plurality of exposing media, each having a size which is smaller than the size of the body, to distinct parts of a radiation image of the body and of a geometrical calibration grid;

generating signal representations of partial radiation images recorded on said exposing media, each of said partial radiation images comprising part of an image of said body and part of an image of said geometrical calibration grid;

correcting said signal representations of the partial images for geometrical distortions so as to obtain signal representations of geometrically corrected partial images; and stitching said geometrically corrected partial images thereby forming a radiation image of said body.

2. A method according to claim 1 wherein geometrically corrected partial images are obtained by subjecting said original partial images to a geometric transformation so that the parts of the radiation image of said geometric calibration grid are restored to the geometry of the geometrical calibration grid and simultaneously the parts of the radiation image of the body are restored to the geometry of the original parts of the radiation image.

3. A method according to claim 2 wherein said geometric transformation is a two-dimensional warping transformation for each pixel being defined by a pixel dependent spatial displacement value and an interpolation scheme.

4. A method according to claim 1 wherein said geometric calibration grid is a geometric Cartesian grid composed of regularly spaced equidistant horizontal and vertical grid lines.

5. A method according to claim 3 wherein said pixel dependent displacement values associated with transformed pixels are determined by spatial differences between the radiation image of said part of the geometric calibration grid and a target grid congruent with said geometric calibration grid.

6. A method according to claim 3 wherein an interpolated value of a transformed target pixel is obtained by cubic B-spline interpolation of a neighbourhood of input pixel gray values.

7. A method according to claim 3 wherein an interpolated value of a transformed target pixel is obtained by linear interpolation of a neighbourhood of input pixel input grey values.

* * * * *